United States Patent [19]

Hainfeld

[11] Patent Number: 5,443,813
[45] Date of Patent: Aug. 22, 1995

[54] LOADING AND CONJUGATING CAVITY BIOSTRUCTURES

[75] Inventor: James F. Hainfeld, Shoreham, N.Y.

[73] Assignee: Associated Universities, Inc., Washington, D.C.

[21] Appl. No.: 711,208

[22] Filed: Jun. 6, 1991

[51] Int. Cl.[6] .............................................. A61K 51/10
[52] U.S. Cl. ................................ 424/1.17; 530/391.3; 530/391.5
[58] Field of Search ................ 424/1.1, 450, 1.17; 530/391.3, 391.5, 400

[56] References Cited

U.S. PATENT DOCUMENTS

| | | | |
|---|---|---|---|
| 4,001,480 | 1/1977 | Shank | 426/96 X |
| 4,196,191 | 4/1980 | Almeida et al. | 424/89 |
| 4,224,313 | 9/1980 | Zimermann et al. | 424/1.1 X |
| 4,261,975 | 4/1984 | Fullerton et al. | 424/450 X |
| 4,269,826 | 5/1981 | Zimmermann et al. | 424/1.1 X |
| 4,289,756 | 9/1981 | Zimmermann et al. | 424/1.1 X |
| 4,610,868 | 9/1986 | Fountain et al. | 424/1.1 |
| 4,652,449 | 3/1987 | Ropars et al. | 424/101 |
| 4,671,954 | 6/1987 | Goldberg et al. | 424/450 |
| 4,728,575 | 3/1988 | Gamble et al. | 428/402.2 |
| 4,735,792 | 4/1988 | Srivastava | 424/1.1 |
| 4,755,375 | 7/1988 | Srivastava et al. | 424/1.1 |
| 4,764,359 | 8/1988 | Lemelson | 424/1.1 |
| 4,871,488 | 10/1988 | Mannino et al. | 264/4.6 |
| 4,935,223 | 6/1990 | Phillips | 424/1.1 |
| 4,971,801 | 11/1990 | Urban | 424/1.1 X |
| 5,068,227 | 11/1991 | Weinshenker | 424/1.1 |
| 5,133,956 | 7/1992 | Garlich et al. | 424/1.1 |
| 5,252,348 | 10/1993 | Schreier et al. | 424/450 |
| 5,358,722 | 10/1994 | Monzyk | 424/489 |

FOREIGN PATENT DOCUMENTS 0038546 10/1981 European Pat. Off. .
0269071 11/1987 Japan .
WO8500751 2/1985 WIPO .

OTHER PUBLICATIONS

Meldrum, et al., *Nature*, 349, 684 (1991).
Foley, et al., *Proceedings of the 45th Annual Meeting of the Electron Microscopy Society of America*, G. W. Bailey, Ed., 760 (1987).
Hainfeld, et al., *Nucl. Med. Biol.*, 17, No. 3, 287 (1990).

*Primary Examiner*—Gary L. Geist
*Assistant Examiner*—Lara E. Chapman
*Attorney, Agent, or Firm*—Margaret C. Bogosian

[57] ABSTRACT

Methods for the preparation and use of a biological delivery system are disclosed. The method of preparation includes the loading of a non-biological material into a biostructure having a load-bearing structure. The method also includes the removal of some of the biostructure's contents and the loading of a non-biological material into the biostructure. The biostructure is biologically compatible with the host, and preferably is derived from the host, the host's species or a related species. The loaded biostructure is used directly, or it can be targeted to specific cells, tissues and/or organs within a host. The targeted biostructure can be used to deliver the non-biological material to a specified tissue, organ or cell within a host for diagnostic, therapeutic or other purposes.

5 Claims, 4 Drawing Sheets

LOADING AND CONJUGATING CAVITY BIOSTRUCTURES

This invention was made with Government support under contract number DE-AC02-76CH00016, between the U.S. Department of Energy and Associated Universities, Inc. The Government has certain fights in the invention.

BACKGROUND OF THE INVENTION

1. Field of the Invention

The present invention relates to a biological delivery system loaded with a non-biological material which has a biologically useful effect.

2. Background of the Related Art

The incorporation of chemicals and certain elements into artificial structures for insertion into a host has long been of interest to members of the medical profession. For example, WO 85/00751 discloses the loading of drugs into liposomes (artificial phospholipid vesicles). WO 85/00751 also discloses that the liposomes can be targeted to specific cells by the incorporation of antibodies to antigens known to be associted with the target cell surface. However, since liposomes are not natural structures, they are subject to certain problems such as immunological rejection. Further, liposomes cannot carry a substantial load and tend to have short storage lives.

Another problem is that liposome-entrapped materials tend to leak when the liposome is placed in contact with body fluids. The liposomes also tend to degrade after contacting body fluids and the liposome contents are released in a short period of time. Further, if a very stable liposome is used in vivo, then the liposomal contents will not be released as needed. As a result, stable liposomes tend to be ineffective carriers of therapeutic substances in vivo.

An additional drawback is that liposomes are internalized by naturally occurring phagocytic cells of the reticuloendothelial system (RES), and, therefore, are rapidly cleared from the system. Accordingly, the entrapped drug is largely ineffective against diseases involving cells other than those associated within the RES. A difficulty inherent in treating cells of the RES is that since the cells of the RES phagocytose liposomes, the liposome (and the drugs entrapped therein) are packaged within lysosomes of the phagocytic cell. Very often the lysosome will contain degradative enzymes which will degrade the entrapped compound or render the entrapped compound inactive.

Attempts have been made to overcome the shortcomings inherent in the use of liposomes for targeted drug delivery. For example, International Application WO 85/00751 discloses a process for the preparation of monophasic lipid vesicles (MPVs). MPVs are lipid vesicles which have a plurality of bilayers. An MPV can encapsulate one or more bioactive agents and can be used in vivo in the treatment of disease. Also, U.S. Pat. No. 4,610,868 to Fountain, et al. discloses lipid matrix carriers which provide for the sustained release of bioactive agents in vivo. Drugs, immunoglobulins or other biological materials may be entrapped within the lipid matrix carder. A disadvantage associated with such lipid vesicle structures is that the lipid structures are not native to the host organism and, therefore, they are subject to immunological rejection.

Efforts have been made to incorporate therapeutic substances into non-lipid structures. For example, U.S. Pat. No. 4,671,954 to Goldberg, et al. discloses hydrophilic protein or polypeptide microspheres for incorporation of therapeutic substances. The microspheres are prepared by dispersing an aqueous solution or dispersion of protein or polypeptide in an organic solvent solution of a high molecular weight polymer to form a stabilized dispersion of microspheres. The microspheres are cross-linked with a polyfunctional cross-linking agent. Proteins, antibodies, enzymes, immunostimulants and other compounds may be covalently attached to the microspheres. The microspheres may be targeted to specific tissues using biospecific affinity ligands and may be loaded with biologically active agents. However, being that the microspheres are foreign to the host, the problem of immunological rejection still exists.

Attempts have also been made to enclose paramagnetic materials into artificial lipid structures for use in nuclear magnetic resonance imaging. For example, U.S. Pat. No. 4,728,575 to Gamble, et al. discloses the use of micellular particles to enhance nuclear magnetic resonance imaging by the enclosure of a paramagnetic material within micellular particles such as phospholipid vesicles. To provide specific targeting, antibodies or other cell recognition targeting agents are attached to the surface of the vesicles. A problem with the micellular particles of Gamble, et at. is that they cannot enclose large amounts of paramagnetic materials and are subject to immunological rejection.

Meldrum, et al. (*Synthesis of Inorganic Nanophase Materials in Supramolecular Protein Cages*, Nature, Vol. 349, 684–687) disclose the use of an apoferritin molecule to form a supramolecular protein cage for the synthesis of inorganic materials in the nanometer dimension. These supramolecular cages are predicted to find applications in catalyses and electro-optical devices. Meldrum, et al. do not relate to or suggest the use of apoferritin in a biological delivery system.

It is, therefore, a desired purpose of the present invention to provide a biostructure having a bioencapsulated non-biological material whose in vivo lifetime and fate are largely determined by the biostructure rather than the material transported therein.

It is a further purpose of the present invention to provide biostructures which have been loaded with a desired non-biological material and which can be introduced into a living system while avoiding any unwanted immune response.

It is yet a further purpose of the present invention to provide biostructures which have been loaded with a toxic non-biological material and which can be introduced into a living system while avoiding or lowering the toxicity of the non-biological material.

It is yet another desired purpose of the present invention to provide a biological delivery system of non-biological materials which can be targeted to predetermined sites within a host.

It is a still further purpose of the present invention to provide a biological delivery system which can provide large amounts of a non-biological material, which has a biologically useful effect, to preselected cells and/or organs.

SUMMARY OF THE INVENTION

These and other purposes are achieved by the present invention which includes the loading of biological structures having a load-bearing pocket or internal structure with a non-biological material, having a desired effect, to form a biological delivery system. These biostructures can be loaded with a desired non-biological material. For example, the apoferritin cavity, which normally carries iron, can be filled with uranium, boron, gadolinium, gold compounds, radioisotopes or other non-biological materials.

Loaded biostructures are particularly well suited for diagnostic and therapeutic purposes. The biostructure can be used to carry large amounts of a compound to a region of interest. The biostructures are biocompatible with the host. Preferably, the biostructures originate from a species related to that of the host. Most preferably, the biostructures originate from the host or originate from an organism of the same species as the host. Since the loaded compounds are bioencapsulated, their in vivo lifetime and fate are largely determined by the surface properties of the biostructure, rather than the non-biological material transported within the biostructure. Hence, the difficulties inherent with immunological rejection of materials which are not native to the host organism are avoided.

In a preferred embodiment, loaded biostructures are attached to biospecific affinity ligands, such as antibodies or antibody fragments. These biospecific affinity ligands can be used to target the payload to specified sites. For example, apoferritin loaded with a radioisotope conjugated to an antitumor antibody could be used for the diagnosis or treatment of cancer. Apoferritin loaded with uranium-235 and attached to an antitumor antibody can be used for neutron capture therapy.

Various methods can be used for the attachment of biospecific affinity ligands, such as antibodies or antibody fragments, to the surface of the biostructures. For example, Fab' fragments can be attached to the exterior surface of the biostructure by reacting the surface of the biostructure with a heterobifunctional crosslinker, m-maleimidobenzoyl-N-hydroxysuccinimide ester (MBS), which reacts with primary amines. The resulting maleimido groups then react with the hinge region sulfhydryl in the Fab' fragment. The proportion of antibody to carrier molecule can be controlled and optimized for the specific application. In addition, there are various other methods for the attachment of biospecific affinity ligands to the surface of a biostructure known to those skilled in the art, and these methods are contemplated as falling within the scope of the present invention.

Several methods can be used to load the desired material into the biostructure. One method involves the precipitation or crystallization of a desired material inside the biostructure. The solvent conditions are then adjusted such that the material will not redissolve. Another method includes the covalent attachment of the compound of interest to a surface of the biostructure.

Alternatively, entire cells may be loaded with the desired non-biological material. For example, erythrocytes may be lysed, washed of their hemoglobin to form "ghosts", and suspended in a reagent material to be encapsulated. The "ghosts" are then resealed and the excess external reagent is removed.

For a better understanding of the present invention reference is made to the following description and figures, the scope of which is pointed out in the claims.

DETAILED DESCRIPTION OF THE INVENTION

Definitions:

As used in this specification and in the claims, the following terms are defined as follows:
a. Biostructure—a naturally occurring biological structure that includes, for example, enzymes, viruses, proteins and cells.
b. Non-Biological Material—a material which does not naturally occur in biological systems, its introduction, however, can be used for a desired purpose in a biological host. The term "non-biological material" includes, for example, pharmaceuticals, uranium, boron, gadolinium, gold compounds, radioisotopes, uranium-235, barium, fluorescent molecules and positron emitting isotopes.
c. Load-Bearing Structure—a naturally occurring structure associated with a biostructure, which either naturally exists or has been created in a biostructure resulting in a cavity, space, pocket or other partially or wholly internalized structure capable of carrying a load such as a non-biological material;

d. Biospecific Affinity Ligand—an agent having an affinity for certain tissues, organs and/or cells. Such ligands include, for example, an antibody or an antibody fragment.

e. Apoferritin—the blood protein ferritin which has its iron content removed to form a load-bearing cavity.

f. Fab'—an antigen binding fragment of an antibody. When an antibody is treated with the enzyme pepsin, it will yield an F(ab')$_2$ fragment consisting of two covalently linked Fab' fragments. Fab' fragments can be produced by treating F(ab')$_2$ with a reducing agent.

Figure 2:
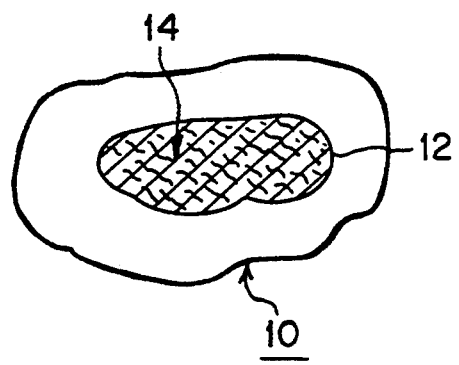
FIG. 2 is a cross-sectional illustration of a biostructure of the present invention having an internal load-bearing structure and an internalized non-biological material.
Figure 4:
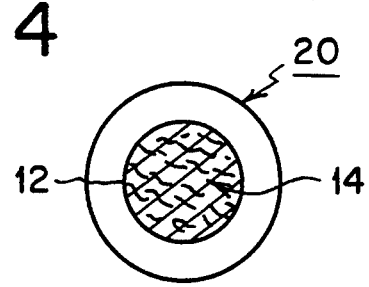
FIG. 4 is a cross-sectional view of an apoferritin molecule of the present invention having internal load-bearing structure and an internalized non-biological material.
Figure 6:
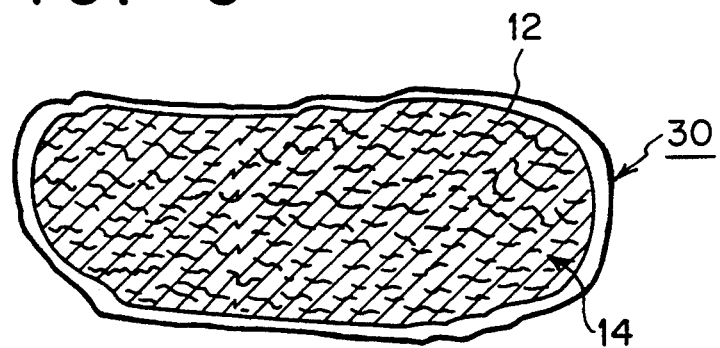
FIG. 6 is a cross-sectional view of a cell of the present invention having an internal load-bearing structure and an internalized non-biological material.
Figure 8:
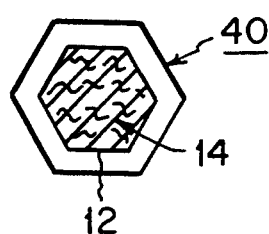
FIG. 8 is a cross-sectional view of a virus of the present invention having an internal load-bearing structure and an internalized non-biological material.
Figure 10:
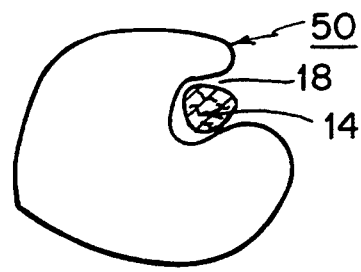
FIG. 10 is a cross-sectional view of a biostructure of the present invention in the form of an enzyme or protein having a partially internalized pocket structure, which is loaded with a non-biological material within the pocket.

The present invention includes the loading of a biological structure or biostructure, as defined above, having a load-bearing structure, including a pocket, interior structure or cavity, with a desired non-biological material to form a biological delivery system. A number of biological structures have a pocket, internal cavity or a load-beating structure of some sort. For example, apoferritin, a blood protein, is spherical in shape and has a large internal cavity. Other examples include viruses which have an internal space for carrying nucleic acid. At the smallest end of the scale some molecules, such as most enzymes, contain a "pocket". At a larger end of the scale, cells have a membrane and sometimes a cell wall structure enclosing the cell's contents. FIG. 2 illustrates a biostructure 10 having a load-bearing internal structure 12 and a non-biological material 14. FIG. 4 illustrates an apoferritin molecule 20 of the present invention having a load-bearing internal structure 12 and a non-biological material 14. FIG. 6 illustrates a cell 30 of the present invention having a load-bearing internal structure 12 and a non-biological material 14. FIG. 8 illustrates a virus 40 of the present invention having a load-bearing internal structure 12 and a non-biological material 14. FIG. 10 illustrates a biostructure 50 of the present invention in the form of an enzyme or protein having a partially internalized pocket structure 18 loaded with a non-biological material 14.

The load-beating interior structures of these biostructures can be loaded with the desired non-biological material. For example, the apoferritin cavity, which normally carries iron, can be filled with uranium, boron, gadolinium, various gold compounds, radioisotopes or other non-biological materials.

Loaded biostructures are particularly well suited for diagnostic and therapeutic purposes. The loaded biostructures can be used to carry large amounts of a non-biological material to a region of interest.

The immune response to such in vivo uses of the present invention is determined to a great extent by the surface of the biostructure. The biostructures are biocompatible with the host. Preferably, the biostructures originate from a species related to that of the host. Most preferably, the biostructures originate from the host or originate from the same species as that of the host. Since the loaded compounds are preferably encapsulated by a biostructure native to the host organism, their in vivo lifetime and fate are largely determined by the nature of the biostructure's outer surface rather than the properties of the material transported in the biostructure's interior. Accordingly, the present invention avoids the potentially serious problems associated with immunological rejection.

Frequently the materials and compounds that might be used for diagnosis and therapy have toxic side effects that result in damage or destruction of healthy tissue in the patient. As a result, some such compounds must be used at less then effective doses and some cannot be used at all. By encapsulating these materials in the load-beating structures of biostructures, their in vivo toxicity can be reduced or eliminated since they are not directly exposed to the body but are either partially or totally "hidden" inside normal body components.

Figure 3:
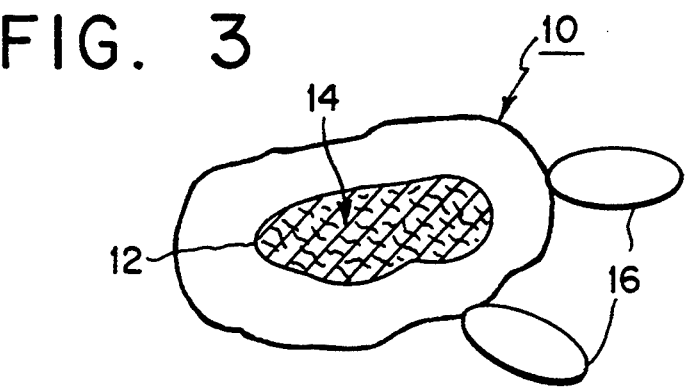
FIG. 3 is a cross-sectional view of a biostructure of the present invention having an internal load-bearing structure, internalized non-biological material, and biospecific-affinity ligands attached to the exterior of the biostructure.
Figure 5:
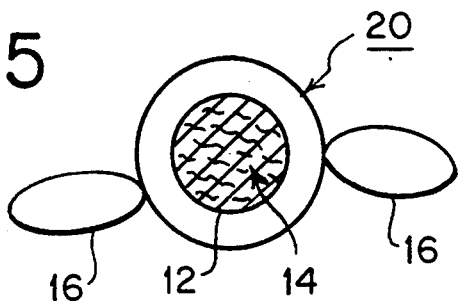
FIG. 5 is a cross-sectional view of an apoferritin molecule of the present invention having an internalized non-biological material and biospecific affinity ligands attached to the exterior of the biostructure.
Figure 7:
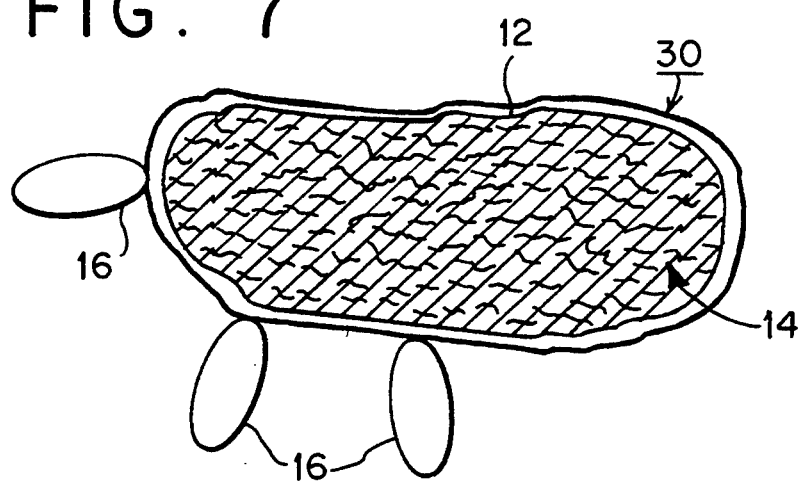
FIG. 7 is a cross-sectional view of a cell of the present invention having an internal load-bearing structure, an internalized non-biological material and biospecific affinity ligands attached to the exterior of the biostructure.
Figure 9:
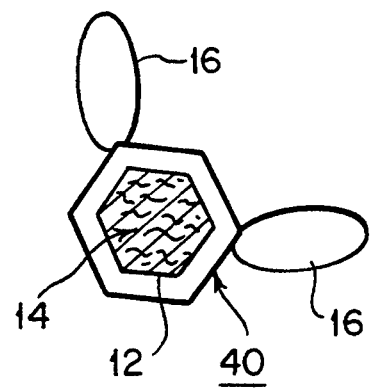
FIG. 9 is a cross-sectional view of a virus of the present invention having an internal load-bearing structure, internalized non-biological material, and biospecific affinity ligands attached to the exterior of the biostructure.
Figure 11:
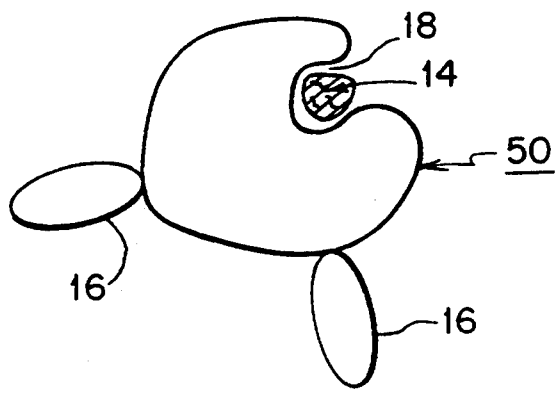
FIG. 11 is a cross-sectional view of a biostructure of the present invention in the form of an enzyme or protein having a partially internalized pocket structure, which is loaded with a non-biological material within the pocket and biospecific affinity ligands attached to the exterior of the biostructure.

In one preferred embodiment, the biostructures are targeted to specific sites within a host. The biostructures can be targeted by attaching biospecific affinity ligands to the biostructure. The biospecific affinity ligands can, for example, include antibodies or antibody fragments specific for antigens on the target site. Suitable biospecific affinity ligands include, for example Fab', F(ab')$_2$ and IgG. FIGS. 3, 5, 7, 9 and 11 illustrate biostructures of the present invention having biospecific affinity ligands 16. FIG. 3 illustrates a biostructure 10 having an internal load-bearing structure 12, a non-biological material 14 and biospecific affinity ligands 16. FIG. 5 illustrates an apoferritin molecule 20 of the present invention having an internal load-beating structure 12, a non-biological material 14 and biospecific affinity ligands 16. FIG. 7 illustrates a cell 30 of the present invention having an internal load bearing structure 12, a non-biological material 14 and biospecific affinity ligands 16. FIG. 9 illustrates a virus 40 of the present invention having an internal load-bearing structure 12, a non-biological material 14 and biospecific affinity ligands 16. FIG. 11 illustrates a biostructure 50 of the present invention in the form of an enzyme or protein having a partially internalized pocket structure 18, a non-biological material 14 and biospecific affinity ligands 16. The biostructure can also be chosen so that it is preferentially taken up at the target site of interest. For example, certain cells of the reticuloendothelial system have a high affinity for certain lipoproteins. In addition, some viruses have a specific affinity for certain types of cells (e.g., some viruses are specific for cells of the central nervous system). The target sites can be, for example, specified organs, cells and/or tumors.

Various methods can be used for the attachment of biospecific affinity ligands, such as antibodies or antibody fragments, to the biostructure. Suitable methods for the attachment of biospecific affinity ligands are known to those skilled in the art and are contemplated to be within the scope of the present invention. For example, Fab' fragments can be attached to the exterior surface of the biostructure by reacting the surface of the biostructure with a heterobifunctional crosslinker that reacts with primary amines. Suitable heterobifunctional crosslinkers include m-maleimido-benzoyl-N-hydroxysuccinimide ester (MBS), sulfosuccinimidyl-4-(N-maleimidomethyl)cyclohexane-1-carboxylate (sulfo-SMCC), and N-succinimidyl-(4-iodoacetyl)aminobenzoate (SIAB). The resulting maleimido groups then react with the hinge region sulfhydryl in the Fab' fragment. The proportion of antibody to carrier molecule can be controlled and optimized for the specific application.

In another preferred embodiment of the present invention, apoferritin is conjugated to an antitumor antibody and loaded with a radioisotope. The antitumor antibody enables the loaded apoferritin to associate with the tumor and the radioisotope loaded apoferritin can, for example, be used for the diagnosis and/or treatment of cancer. Currently, only 1 to 3 radioisotope atoms can be attached to an antibody without affecting the antibody's immunoreactivity. The present invention can be used to load apoferritin with approximately 5,000 radioisotope atoms. The loaded apoferritin can then be conjugated to antibodies without significant loss of immunoreactivity. The high loading capability is considered to be one of the significant elements of the present invention.

Several methods can be used to load the biostructure with a biologically useful material. One method includes the precipitation or crystallization of the nonbiological material inside the biostructure. Another method includes the diffusion of the non-biological material into the interior of the biostructure, and the chemical attachment of the non-biological material to the internal surface of the biostructure. The chemical attachment can be achieved, for example, by adjustment of pH to a reaction range sufficient for covalent coupling, or exposure to ultra violet or visible light to initiate photo-crosslinking. The appropriate conditions depend primarily upon the nature of the non-biological material and the nature of the biostructure. Preferably, a cross-linking reagent is attached to the biostructure and then attached to the non-biological material.

If desired, the non-biological material can be polymerized within the biostructure. In this process, reactants are diffused into the biostructure and polymerization is initiated by application of the appropriate stimuli. The appropriate stimuli will depend upon the nature of the non-biological material and can include, for example, chemical initiators, adjustment of pH, or ultra-violet or visible light. Since the nucleation sites and the reactants are contained in the cavity, the polymer assembles internally. One advantage of polymerization is the formation of a more stable form of the included material, which will not diffuse out or otherwise escape from the cavity or pocket of the biostructure.

Still another method includes the lysing of biostructures, such as erythrocytes to form "ghosts", and the suspension of the lysed biostructure in the material to be encapsulated. The lysed biostructures are resealed under appropriate conditions and encapsulate the non-biological material. If desired, the non-biological material can be chemically attached to the interior surface of the biostructure as previously described.

There are numerous applications for the present invention. The present invention is particularly useful with Neutron Capture Therapy. A neutron is an uncharged sub-atomic particle. Certain elements such as boron-10 and uranium-235 absorb neutrons. The absorption of neutrons by boron-10 results in the production of alpha particles, which have the ability to kill cells. Neutron capture therapy is particularly useful for the treatment of tumors. Until now, it has not been possible to link enough boron or uranium to antibodies to permit successful Neutron Capture Therapy.

In performing Neutron Capture Therapy according to one preferred embodiment of the present invention, the biostructure is conjugated to a biospecific affinity ligand, and the cavity of the biostructure is loaded with boron-10 or uranium-235. The loaded biostructure is introduced into a host and associates with the target. In an alternative embodiment, the biostructure is preferentially taken up by cancer cells. A neutron beam is directed at the target causing the boron-10 to emit alpha particles, which destroy the target cells. When uranium-235 is used, the neutron beam causes fission of the uranium and the resulting emission of highly energetic particles, which destroy the target cells.

The present invention can also be used with radioimmunotherapy and radiotherapies. In such therapies radioisotopes are incorporated within the interior or pocket of a biostructure. The outer surface of the biostructure either naturally contains biospecific affinity ligands or such ligands are attached. The affinity ligands are specific for targeted cells. Alternatively, the biostructures can be of a type which is preferentially taken up by the particular targeted cells or organs. The present invention provides an increase in the effectiveness of radiotherapies and radioimmunotherapies by increasing the number of radioisotopes associated with each biospecific affinity ligand.

Another use for the present invention is in the field of radioimaging. In this embodiment, radioisotopes are placed within the interior of the biostructure. The biostructure may also be targeted to an area of interest by the attachment of biospecific affinity ligands and/or by use of biostructures which are preferentially taken up at the area of interest. The biostructure is introduced into the host and can be used, for example, to track the vascular system, to label tumors and to label blood clots.

The present invention can provide non-toxic x-ray contrast agents and also deliver these agents to specified targets. Barium or other appropriate reagents can be loaded into the biostructure and the biostructure may also be targeted to a region of interest.

Yet another use for the present invention is in the field of x-ray induced fluorescence. Certain elements fluoresce upon exposure to x-ray wavelengths. These elements can be encapsulated within a targeted biostructure. The biostructure is introduced into the host and associates with the area of interest. The area of interest is exposed to x-rays causing the encapsulated elements to fluoresce. This process is very sensitive and can be used, for example, to detect small tumors.

The present invention also has applications in Magnetic Resonance Imaging (MRI). Gadolinium or other appropriate paramagnetic atoms can be placed within the interior of a biostructure. The biostructure can be targeted to specified areas as previously described. MRI can then be used to selectively and noninvasively provide images of targeted areas of the human anatomy. The present invention could be used, for example, for the non-invasive detection of small tumors if the biostructure is attached to an antitumor antibody, and the biostructure is loaded with a non-biological material having paramagnetic atoms. Previously, it has not been possible to target enough gadolinium per antibody to permit tumor visibility using MRI.

The present invention is especially useful for fluorescent detection. The present invention can be used to increase the sensitivity of fluorescent testing methods many fold. According to this embodiment, fluorescent molecules are incorporated into a biostructure. Hundreds or thousands of fluorescent molecules can be loaded into the biostructure, and the biostructure can be targeted by attachment of a biospecific affinity ligand. Having hundreds or thousands of fluorescent molecules per antibody would provide a tremendous proportional improvement in sensitivity over the one fluorescent molecule per antibody that is now commonly used. Diagnostic tests for AIDS and other disorders can be simplified and made more reliable. In this manner, the present invention can tremendously increase the sensitivity of fluorescent antibody assays.

The present invention can also be used with Positron Emission Tomography (PET). PET is typically used to measure the physiological functioning of organs and related biochemical processes. PET is also used to provide three dimensional images of internal structures and organs. Using the present invention, specific areas of the body could be targeted and studied. For example, the cavity of an apoferritin protein is loaded with a positron emitter and targeted to a tumor by attachment of an antitumor antibody to the surface of the protein. This permits a PET scan of the tumor to attain a localized image of the tumor.

The present invention is also useful with analytical tools such as X-ray CAT scanning, electron microscopy, energy loss spectroscopy, energy dispersive x-ray, Auger and light microscopy. For example, energy dispersive x-ray microanalysis could detect apoferritin loaded with gold with almost no background.

Accordingly, the present invention provides several advantages:
1. It greatly increases the sensitivity of antibody assays.
2. The biological delivery system of the present invention is biocompatible with the host and avoids the problems associated with immunological rejection. The immunological response is determined by the surface of the biostructure and not the internalized non-biological material. Previous techniques have exposed and introduced new moieties which were frequently immunogenic, metabolized by the liver and/or exhibited unwanted uptake in non-target tissues when used in vivo.
3. The biological delivery system of the present invention avoids the problems of toxicity. Because the material to be delivered is either fully or partially encapsulated in a normal biological structure, any toxic effects of the material are either completely hidden or at least reduced.
4. It offers flexibility, since a wide variety of biostructures can be utilized with the present invention. Suitable biostructures include enzymes, storage proteins, viruses and cells. Numerous compounds can be used as the non-biological material. These compounds can be mixed to yield "cocktails" of, for example, radioisotopes or other substances designed for a specific application. This flexibility gives the physician a wide range of treatments and methods.
5. It permits the delivery of the non-biological materials to selected cells, tumors and/or organs.
6. It permits the loading of a large amount of a non-biological material into a biostructure.

EXAMPLES

Example 1

The Loading of Apoferritin with Uranium A 0.4 mg aliquot of apoferritin was treated with a 1M sodium phosphate buffer (pH 9) for 4 hours at room temperature. The apoferritin was then applied to a 0.66×50 cm GH25 column (AMICON—Beverly, Mass.) running at 2 ml/min, and eluted with deionized water to remove the external buffer. A 0.03% uranyl acetate solution (1.0 ml) was added to 1.0 ml of the peak apoferritin fraction. The uranyl acetate diffused into and precipitated within the apoferritin cavity. After 1 hour, 2.0 ml of 0.1M sodium phosphate buffer (pH 7.0) was added. One hour later, the solution was filtered through a 0.1μ filter, concentrated with a CENTRICON-30 device (AMICON) and chromatographed on a 0.66×50 cm GH25 column running in 0.1M sodium phosphate (pH 7.0) buffer.

Uranyl acetate precipitates in the presence of a sufficient concentration of phosphate ions and at higher pHs. Typically, uranyl acetate precipitates at a pH of about 5 and above.

The uranyl ion precipitates and crystallizes due to the presence of the high pH and phosphate ions within the apoferritin cavity. The phosphate ions were introduced to the cavity by the treatment of the apoferritin with phosphate buffer. The UV visible spectrum of the loaded apoferritin is considerably different from native apoferritin and quantitative analysis indicated up to 1,000 uranium atoms per apoferritin molecule. The presence of uranium was confirmed by quantitative electron microscopy and direct current plasma spectroscopy elemental analysis.

Figure 1:
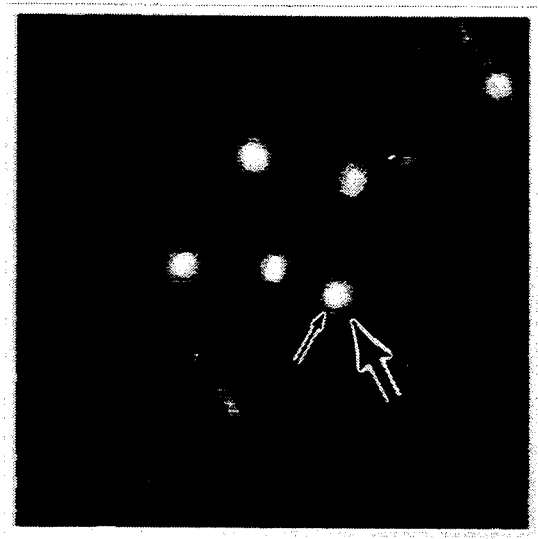
FIG. 1 illustrates a scanning transmission electron micrograph of apoferritin (round objects indicated by the thin arrow) in a 128 nm wide scan-field.

The loading of 1,000 uranium (U-238) atoms into an apoferritin protein structure has been achieved with this method. The loaded uranium salt can be rendered insoluble by adjusting the pH to about 7.4. FIG. 1 is an electron micrograph of 5 apoferritin protein biostructures loaded with uranium. The uranium is represented by the bright, dense cores.

Example 2

Coupling of Fab' Antibody Fragments to Uranium-Loaded Apoferritin

Free thiols on the uranium-loaded apoferritin were first blocked by reaction with 100 molar excess of N-ethylmaleimide. The crosslinker sulfo-SMCC was reacted in 20 molar excess in 0.1M Hepes (pH 7.4) buffer for 1 hour at room temperature. After purification on a gel exclusion column, an 8 fold molar excess of goat anti-mouse Fab' was added at pH 7.0 and incubated overnight. The sample was then purified on a SUPERDEX 75 column (HR10, PHARMACIA-LKB Biotechnology, Piscataway, N.J.). The uranium-loaded apoferritin showed Fab' attachment by electron microscopy and polyacrylamide gel electrophoresis. Almost 100% of the sample bound to a mouse IgG affinity column, thus demonstrating targeting of the loaded biostructure.

While there have been described what are the presently contemplated preferred embodiments of the invention, those skilled in the art will realize that various changes and modifications may be made to the invention without departing from the spirit of the invention, and it is intended to claim all such changes and modifications as falling within the scope of the present invention.

I claim:

1. A biological delivery system comprising apoferritin, said apoferritin having a load-bearing structure and being biologically compatible with a host, said load-bearing structure loaded with uranium-235 and conjugated to biospecific affinity ligand.

2. The delivery system of claim 1 wherein said apoferritin is derived from an organism of the same genus as that of the host.

3. The delivery system of claim 1 wherein said apoferritin is derived from an organism of the same species as that of the host.

4. The delivery system of claim 1 wherein said apoferritin is derived from the host.

5. The delivery system of claim 1 wherein said uranium-235 is used for neutron capture therapy.

* * * * *